United States Patent
Bounouar et al.

(10) Patent No.: US 8,462,335 B2
(45) Date of Patent: Jun. 11, 2013

(54) SYSTEM FOR ANALYZING A LOW-PRESSURE GAS BY OPTICAL EMISSION SPECTROSCOPY

(75) Inventors: Julien Bounouar, Annecy (FR); Smail Hadj-Rabah, Annecy (FR)

(73) Assignee: Alcatel Lucent, Paris (FR)

( * ) Notice: Subject to any disclaimer, the term of this patent is extended or adjusted under 35 U.S.C. 154(b) by 268 days.

(21) Appl. No.: 12/733,371

(22) PCT Filed: Jul. 22, 2008

(86) PCT No.: PCT/EP2008/059614
§ 371 (c)(1), (2), (4) Date: May 10, 2010

(87) PCT Pub. No.: WO2009/027156
PCT Pub. Date: Mar. 5, 2009

(65) Prior Publication Data
US 2010/0277724 A1    Nov. 4, 2010

(30) Foreign Application Priority Data
Aug. 27, 2007 (FR) .................................... 07 57203

(51) Int. Cl.
G01J 3/30 (2006.01)
(52) U.S. Cl.
USPC ........................................................ 356/316
(58) Field of Classification Search
USPC ................................... 356/300–334
See application file for complete search history.

(56) References Cited

U.S. PATENT DOCUMENTS 2,457,781 A * 12/1948 Metten et al. .................... 313/93
3,382,389 A    5/1968 Schaedler
(Continued)

FOREIGN PATENT DOCUMENTS

GB     2 441 582       3/2008
GB     2441582 A *     3/2008
(Continued)

OTHER PUBLICATIONS

Reiss, K.H.; Die Lichtemission von Hochvakuumgasentladungen; Zeitscrift Fur Angewandte Physik; vol. 7, 1955, pp. 433-437; XP008090968; Allemagne.
(Continued)

*Primary Examiner* — Gregory J Toatley
*Assistant Examiner* — Dominic J Bologna
(74) *Attorney, Agent, or Firm* — Carmen Patti Law Group, LLC

(57) ABSTRACT

The object of the invention is a system for analyzing gases which are at a pressure on the order of a secondary vacuum. The system includes a gas ionization device that includes a cathode having conducting walls defining a cylindrical volume and a disc including at least one central through hole, an anode placed substantially at the center of the hole, a plasma source, the plasma being generated in the cylindrical volume by the combined action of an electric field and a magnetic field, orthogonal to the electric field, a system for collecting the light radiation emitted by the plasma, a cylindrical cavity coaxial to the anode having a conductance lower than that of the cylindrical volume and arranged between the ionization device and the collector system, and an analysis device for the ionized gases including an optical spectrometer for analyzing the evolution of the radiating spectrum. Preferably, the end of the cavity opposite the cylindrical volume is closed by a window that is transparent to the light radiation emitted by the plasma.

10 Claims, 4 Drawing Sheets

U.S. PATENT DOCUMENTS

Figure 6:
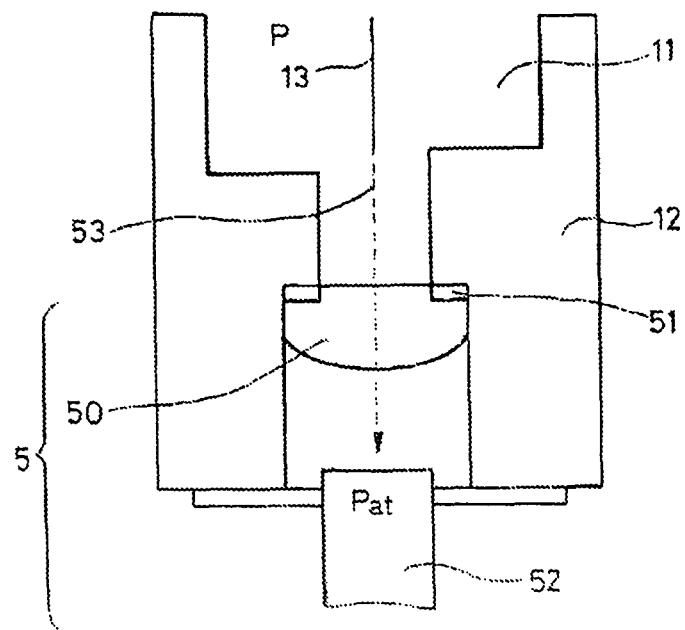

| | | | |
|---|---|---|---|
| 6,366,346 B1 * | 4/2002 | Nowak et al. | 356/72 |
| 6,503,364 B1 | 1/2003 | Masuda et al. | |
| 6,881,971 B2 * | 4/2005 | Ahmad | 250/504 R |
| 6,894,298 B2 * | 5/2005 | Ahmad et al. | 250/504 R |
| 2002/0140932 A1 | 10/2002 | Satou et al. | |
| 2003/0190012 A1 | 10/2003 | Ahmad | |
| 2004/0179187 A1 * | 9/2004 | Mettes | 356/72 |
| 2006/0290925 A1 * | 12/2006 | Nomine et al. | 356/316 |

FOREIGN PATENT DOCUMENTS

| | | |
|---|---|---|
| JP | 6120169 | 4/1994 |
| JP | 2000124199 | 4/2000 |
| WO | WO 00/31773 | 6/2000 |

OTHER PUBLICATIONS

Beck, A.H. et al; A Cylindrical Magnetron Ionisation Gauge; Vacuum, vol. 2, 1952, pp. 137-146; XP002478311.

* cited by examiner

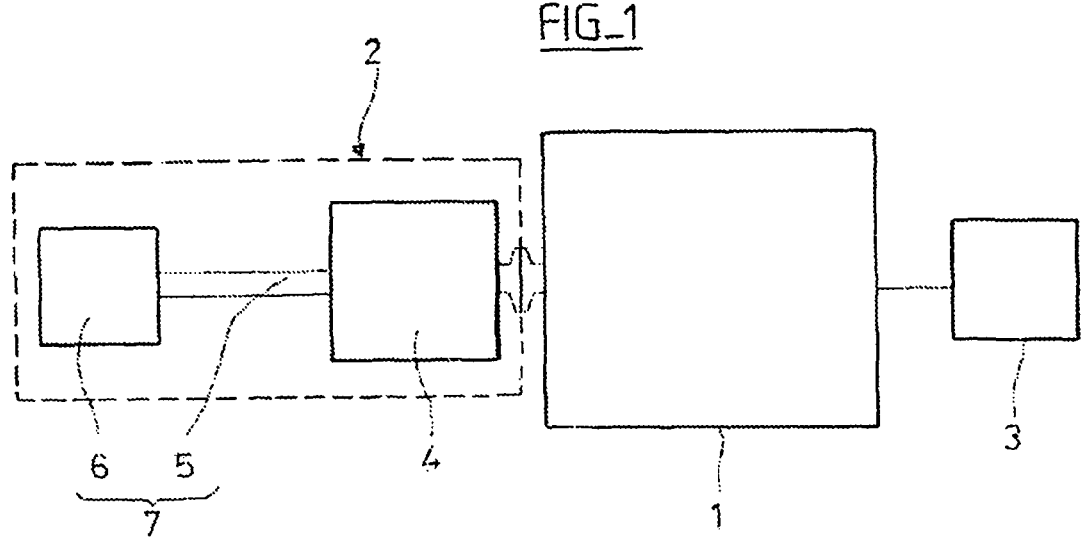
FIG_1
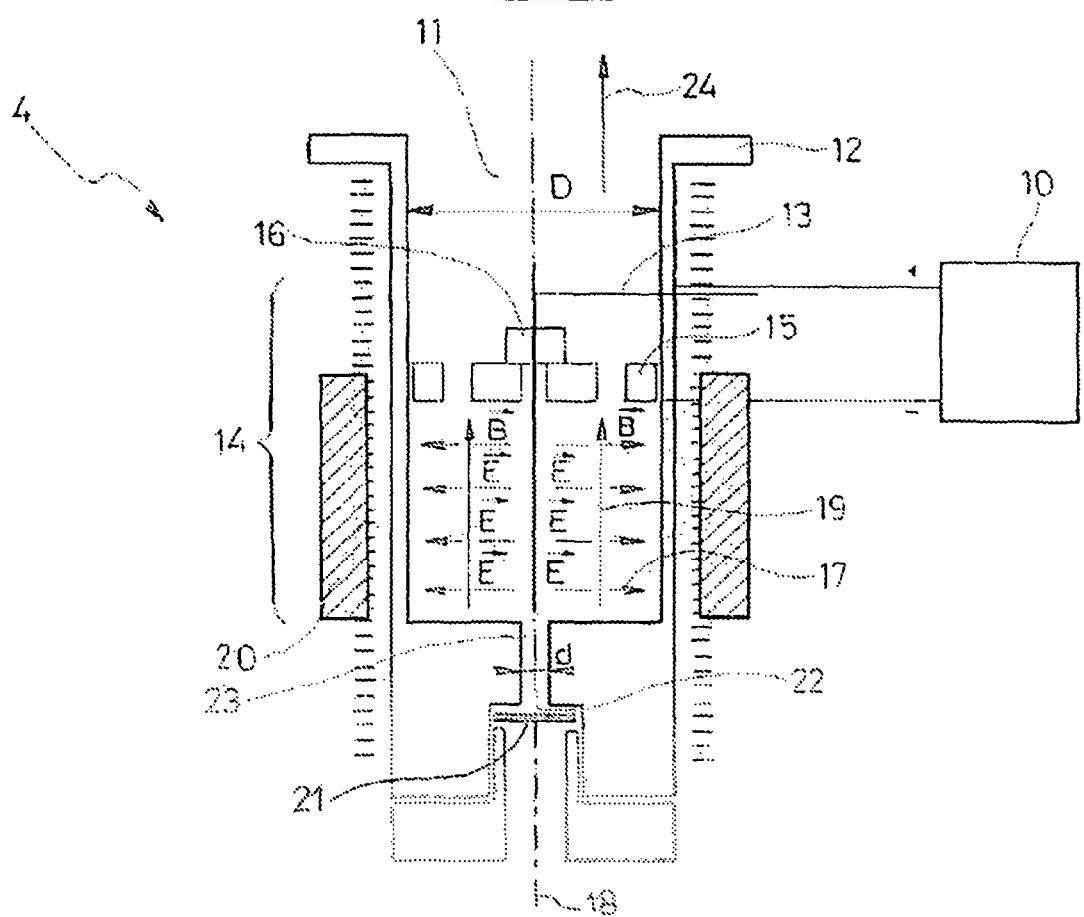
FIG_2

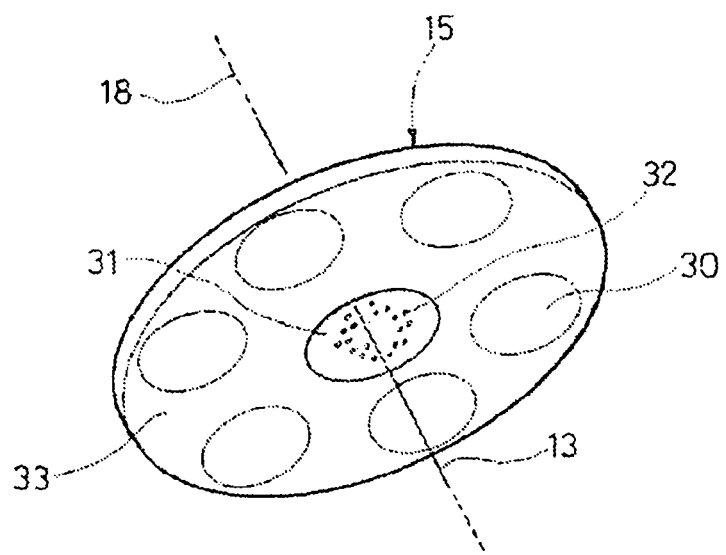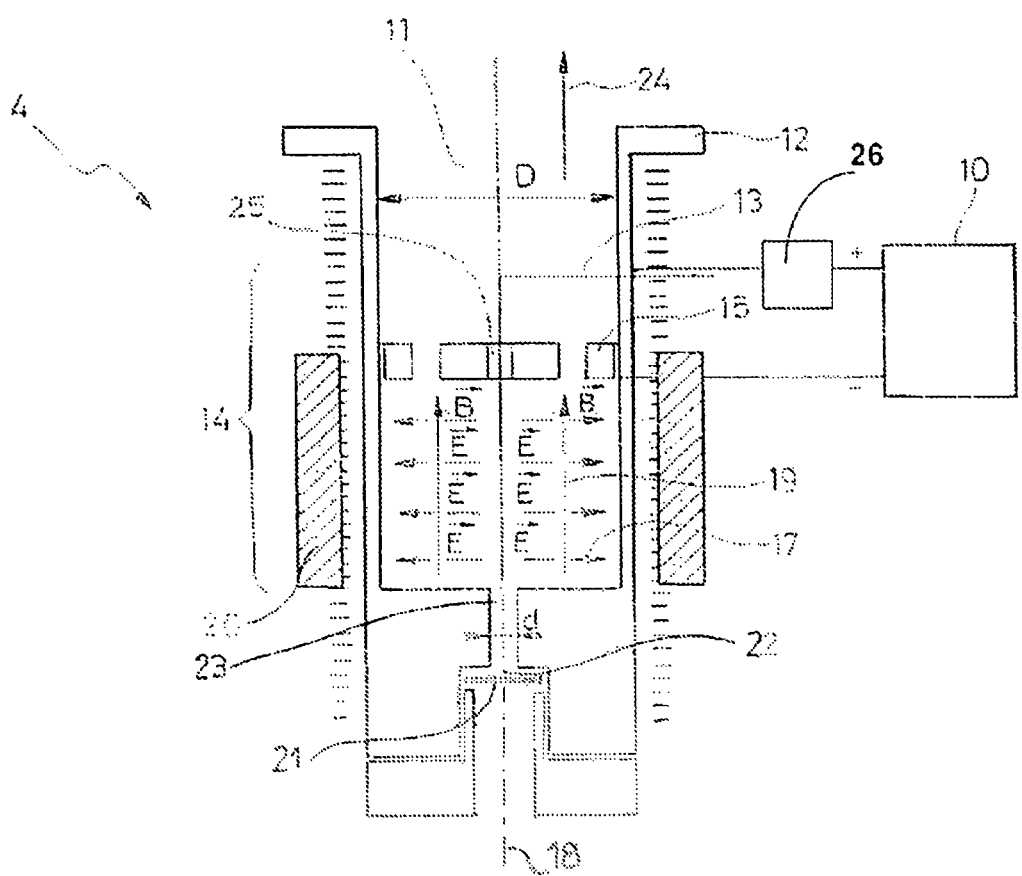

FIG_5
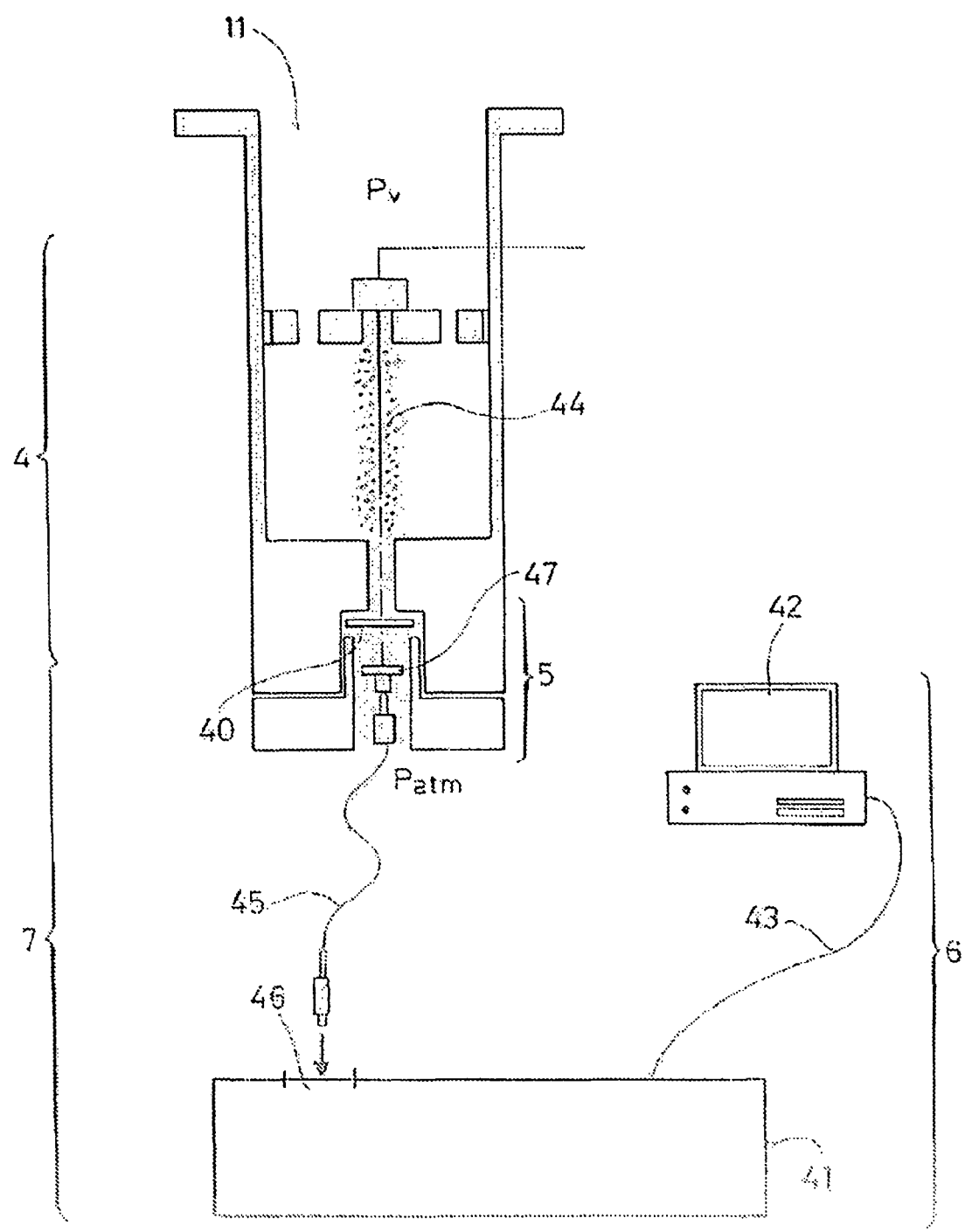

SYSTEM FOR ANALYZING A LOW-PRESSURE GAS BY OPTICAL EMISSION SPECTROSCOPY

The invention relates to a system for analyzing very low-pressure gases, on the order of a secondary vacuum ($10^{-3}$ and $10^{-8}$ mbar), using optical emission spectroscopy. The invention further relates to a method for analyzing gas effluents originating from within a controlled-pressure enclosure. Lastly, the invention discloses an industrial device comprising at least one controlled-pressure enclosure, and a gas-analyzing system cooperating with the controlled-pressure enclosure.

The progress achieved over the past few years in the semiconductor industry has primarily been linked to the increasing integration of electronic circuits on components several square millimeters in size, which is occurring on increasingly large silicon wafers (with diameters of 200 mm to 300 mm).

The technological steps needed to create such circuits are many in number (up to 400). Among them, the steps of vacuum processing play an essential role, both due to their abilities to produce continuously throughout the fabrication process and due to their capabilities to abide by the component's geometric criteria.

The implementation of an on-site process analysis method identifies faults as soon as they have been created, reducing the reaction time during which a large number of batches may be produced. As a result, significant demand is appearing for tracking and controlling semiconductor fabrication processes on-site in real time using plasma, produced in a vacuum.

The use of optical emission spectroscopy in semi-conductor fabrication devices is known. Emission spectroscopy is used to detect the end of the attack in circuit-etching or semiconductor component-etching processes. The plasma analyzed is that generated by the device's reactor. The device is simply equipped with an emission spectrometer that analyzes the light from the etching process, enabling a check of the steps of the process by itself.

However, the aim is to use optical emission spectrometry to check not the steps of the semiconductor device's fabrication or etching process, but rather all of the gases that make up the device's vacuum environment. An optical emission spectrometer, after scattering light, analyzes in real time the change in the radiation emitted by the atoms, molecules, and ions excited by the plasma's free electrons.

However, currently known techniques only enable such measurements in a rough vacuum (from 1000 mbar to 1 mbar) or in a primary vacuum (from 1 mbar to $10^{-3}$ mbar).

The document EP-1,022,559 describes a device comprising an enclosure containing gases at a pressure between 0.1 mbar and 1000 mbar, and a system for analyzing these gases comprising a gas-ionization device and a gas-analyzing device using optical emission spectroscopy. The ionization device comprises a radio-wave source of plasma, which is an ICP or microwave source.

The document EP-1,131,670 describes a device that uses optical emission spectroscopy to check gas specimens originating from within an enclosure. The device comprises a chamber comprising a plasma-formation area and a means for analyzing the light radiation emitted by the plasma. A radiation sensor, such as an optical fiber, is placed near the plasma-formation area. The plasma is formed by means of a power generator associated with an excitation antenna generating electromagnetic waves. An electrical or magnetic field is used to form a barrier in order to separate the ionized particles from the radiation-transparent interface.

The document WO-00/31,773 describes a device for determining the composition of a gas effluent originating from within a vacuum process chamber. The device comprises a cell in which the plasma is formed and a detector, placed behind a window, for collecting the light emitted by the plasma and transmitting it to an optical spectrum analyzer. The plasma is generated by an electrical field produced by an alternating current generator, such as a commercial generator of the sort used in fluorescent lamps or a magnetron microwave generator. In one particular embodiment, a solid cathode is disposed coaxially in the direction of the gas flow and isolated from the conductive wall of the cell used as the anode.

Once the pressure in the process chamber drops below $10^{-3}$ mbar, current systems are no longer capable of sufficiently exciting the gases in order to generate usable light for spectroscopic measurement. The problem is therefore to generate light radiation emitted from a plasma that is sufficiently luminous and sufficiently concentrated to make it possible to analyze, in real-time (less than one second), gas specimens in a secondary vacuum (from $10^{-3}$ to $10^{-7}$ mbar) using optical emission spectrometry.

However, this measurement must also be reproducible throughout the entire duration necessary for the analysis.

The object of the invention is a system for analyzing gases under pressure on the order of a secondary vacuum. The analysis system includes a gas-ionization device comprising
  a cathode having conducting walls defining a cylindrical volume and a disc including at least one central through hole,
  an anode placed substantially at the centre of the hole,
  a plasma source, the plasma being generated in the cylindrical volume by the combined action of an electric field and a magnetic field orthogonal to the electric field,
 a system for collecting the light radiation emitted by the plasma,
 a cylindrical cavity coaxial to the anode, having a conductance lower than that of the cylindrical volume, arranged between the ionization device and the collector system, and
 an analysis device for the ionized gases including an optical spectrometer for analyzing the evolution of the radiating spectrum.

The anode must be centered in the central hole of the disc, otherwise, the ring of light would not be created and measurement would be impossible at low pressure.

More precisely, the cathode comprises a perforated disc comprising peripheral transverse holes surrounding the transverse central hole.

According to one embodiment of the invention, the diameter d of the cavity is less than the diameter D of the cylindrical volume, and it is adjustable in accordance with the pressure of the gas to be analyzed.

According to another embodiment of the invention, the anode is insulated from the cathode by a mount made of dielectric material attached to the disc of the cathode.

According to yet another embodiment of the invention, the anode is insulated from the cathode by a mount made of dielectric material inserted in the central hole of the disc of the cathode.

Advantageously, in this latter case, the system further comprises a regulating device making it possible to control the supply voltage of the anode upon variation of the pressure of the gases to be analyzed.

The collecting system comprises at least one converging lens, which is disposed such that the optical axis of the lens and the axis of the electrodes are preferentially one and the same.

According to one variant, the end of the cavity opposite the cylindrical volume is blocked by a window transparent to the light radiation emitted by the plasma.

According to another variant, the end of the cavity opposite the volume is blocked by a lens transparent to the light radiation emitted by the plasma. In this situation, the lens also fulfils the function of the window.

In order to minimize the pollution of the window or the lens, the cavity is preferentially disposed at the end of the cylindrical volume so that the path of the light radiation which crosses through it goes in the same direction, opposite the flow of the pumped gases.

A further object of the invention is a plasma-based semiconductor fabrication device comprising at least one enclosure containing gases kept in a secondary vacuum, connected to the gas-analyzing system described above. The gas-analyzing system comprises a device for analyzing ionized gases, comprising an optical emission spectrometer and the computer. According to the invention, the optical emission spectrometer and the computer are placed within a shared casing, so as to constitute a compact integrated control system, and they are connected to the device in order to interact with it depending on the results of the gas analysis.

Other characteristics and advantages of the present invention will become apparent upon reading the following description of one embodiment, which is naturally given by way of a non-limiting example, and in the attached drawing, in which:

FIG. 1 schematically depicts an industrial machine comprising an inventive gas-analyzing system, FIG. 2 shows the gas-ionization device according to one embodiment of the invention, FIG. 3 is a detailed view of the disc of the gas-ionization device's cathode, FIG. 4, similar to FIG. 2, shows the gas-ionization device according to another embodiment of the invention, FIG. 5 depicts the optical acquisition chain of the ionized gas analyzing system, FIG. 6 is a detailed view of the area collecting the light radiation emitted by the plasma.

The industrial device depicted in FIG. 1 comprises at least one enclosure 1, whose pressure is controlled, and a gas-analyzing system 2 communicating with the enclosure 1. A secondary vacuum Pv (from $10^{-3}$ to $10^{-8}$ mbar) is built into the enclosure 1 by means of a vacuum line comprising a primary and secondary pumping unit 3. The gas-analyzing system comprises a gas-ionization device 4 that ionizes by means of a source of plasma, and an optical collector system 5 which makes it possible to collect the light and route it towards an analysis device 6. The optical collector 5 and the analysis device 6 form an optical acquisition chain 7.

FIG. 2 more accurately shows the gas-ionization device 4 of the gas-analyzing system 2 according to the invention. The ionization device 4 comprises a source of plasma and direct current generator 10.

The ionization device 4 comprises a cylindrical volume 11, with diameter D and which is delimited by walls 12 made of a vacuum-resistant conductive material, such as stainless steel. The ionization device 4 is connected to the enclosure 1 placed into a secondary vacuum. The volume 11 may be vacuumized using pumping means 3 of the enclosure 1, which is itself vacuumized. A plasma is generated within this volume 11 in order to make it possible to analyze the gas specimens found within the enclosure 1.

The source of plasma is formed of an anode 13 (+ pole) and a cathode 14 (− pole) respectively connected to the positive and negative polls of the direct current generator 10. The cathode 14 comprises walls 12 that delimit the cylindrical volume 11 of diameter D, and a perforated disc 15. The anode 13 is a wire anode, and is placed at the center of the cathode 14 from which it is insulated by a mount 16 made of a dielectric material with a low degassing rate, such as a ceramic, positioned on the surface of the disc 15 of the cathode 14.

The generator 10 applies between the (positively charged) anode 13 and the (negatively charged) cathode 14 a great difference in potential, on the order of 3000 Volts, which generates an intense electrical field E 17 in a transverse direction in relation to the axis 18 of the source of plasma. This field 17 makes it possible to create a plasma by generating and accelerating a flow of electrons from the cathode 14 to the anode 13 in order to excite and ionize the gas molecules originating from within the enclosure 1. In order to achieve usable plasma, a magnetic field B 19 with constant intensity, about 100 mT, and a given direction, perpendicular to the electrical field 17 and parallel to the axis 18 is added to it. The magnetic field 19 is generated by at least one toroid permanent magnet 20 surrounding the cylindrical volume 11. The presence of a magnetic field B 19 coupled to the electrical fields E 17 makes it possible to heavily increase the excitation of the plasma's gas molecules. Thus, the source of plasma is generated by the combined action of a constant electrical field 17 between two geometrically cylindrical electrodes 13, 14 and a constant magnetic field 19 parallel to the surface of the electrodes 13, 14 and orthogonal to the electrical field 17.

Formed plasma is used as a source of light. The light emitted, coming from the de-excitation of the molecules characteristic of the gases which are present, thereby becomes enough to enable a real-time measurement (less than 1 second) in a secondary vacuum.

However, the generation of a plasma in a vacuum within the volume 11 causes molecular cracking in the molecules (particularly hydrocarbons) which are present within the vacuumized enclosure 1 whose gases need to be analyzed. Once cracked, these molecules tend to adhere onto the walls 12 of the volume 11 where the plasma is being created with tight bonds, and are therefore difficult to dislodge. In this situation, the source of plasma serves to trap these molecules, and thereby contributes to decontaminating the enclosure and the pumping lines. However, the presence of this trap is harmful for the optical analysis device.

In order to gather enough light to enable the detection and significant analysis of the gases present within the enclosure 1, it is essential to reduce the distance between the plasma and the analysis device, which causes this device to become rapidly polluted, rendering it opaque to light. Correct measurement quickly becomes difficult, if not impossible, and cannot be reproduced under the same conditions.

In order to remedy this problem, the invention proposes placing a window 21 making it possible to allow through the light emitted by the plasma at the end 22 of a cylindrical cavity 23 opposite the end of the cavity adjacent to the plasma source within the volume 11. The cylindrical cavity 23 has lower conductance than that of the cylindrical volume 11 in which the source of plasma is placed. For example, the cavity 23 may have a diameter d less than the diameter D of the volume 11. For another example, the cavity 23 may have a length greater than or equal to 1 cm and a diameter d which is at least twice as small as the diameter D of the volume 11.

Preferentially, the diameter d of the cavity 23 can be adjusted depending on the working pressure: the greater the working pressure is and the more pollution areas, the smaller the diameter d of the cavity 23 must be. In practice, the diameter d of the cavity 23 is built from the outside with the maximum value compatible with the operation of the low-pressure gas analysis device. Next, depending on the increase in the working pressure, inserts of the same shape as the interior of the cavity may be forced into the cavity 23 so as to reduce its diameter d.

Inside this cavity 23, there is no electrical field E or magnetic field B. The distancing of the window 21 from the source of plasma and the absence of fields within the cavity 23 make it possible to trap the polluting molecules before they reach the window 21. In order to minimize the problem of polluting the window 21, the cavity 23 is advantageously disposed such that the pathway of the light radiation is in the same direction, opposite the flow of the pumped gases 24. A drop in pressure is generated by the vacuumized enclosure's 1 pumping unit 3, within which are the gases to be analyzed, and simultaneously, the plasma causes a slight increase in pressure. The resulting difference in pressure causes a particle flow of the plasma's products towards the pumping unit 3, thereby limiting the pollution of the window 21.

According to one variant embodiment, external heating (not shown) may be added around the cavity 23, which will create a heat-scattering effect for the centrifuge molecules within the cavity 23, and further improve the barrier effect related to the low conductance of the cavity 23.

However, the light emitted by the plasma becomes lower as the pressure of the gases to be analyzed within the enclosure 1 decreases. Additionally, the plasma is scattered across the entire length of the anode 13, which makes it difficult to focus the emitted light onto the analysis device 6. FIG. 3 shows in detail an embodiment of the disc 15 of the cathode 14 making it possible to remedy this drawback.

The cathode 14 comprises a disc 15 pierced with a series of transverse holes 30 on its periphery forming a ring surrounding a central hole 31 which is also transverse. The wired anode 13 transverse the hole 31 at its centre. The use of a perforated disc 15 enables the vacuumizing of this portion of the installation while freeing the circulation of gas molecules.

In this arrangement, the plasma is located within the central hole 31 of the disc 15 in the form of a ring 32 several millimeters in radius centered around the axis 18 and surrounding the anode 13. The obtained located plasma is much more intense, and therefore easier to focus onto the analysis device 6. Thus, an analysis using optical emission spectrometry may be carried out at very low pressures, less than $10^{-3}$ mbar and even $10^{-7}$ mbar.

The magnetic field B 19 is arranged along the generators in revolution cylinder centered on the axis 18 and preferably passes though the material forming the disc 15, which makes it intense in the solid parts 33 of the disc 15 and much weaker in the holes 30, 31 of the disc 15. The use of a disc 15 heavily and locally increases the value of the electrical field E 17 (up to fivefold) as well as the intensity of the magnetic field B 19 within the central hole 31.

During the operation of assembling the ionization device 4 according to the invention, the disc 15 of the cathode 14 is placed perpendicular to the walls 12 of the cylindrical volume 11. The mount 16 is fastened above the disc 15 of the cathode 14. The anode 13 is built in above the disc 15 of the cathode 14, and is joined to the center of the mount 16 so as to be perpendicular to the plane of the disc 15 and to be positioned on the center of the disc 15 of the cathode 14.

The anode 13 must be substantially centered within the disc's central hole. Otherwise, the ring of light 32 is not created and measurement at low pressure is impossible. The centering of the anode 13 within the disc 15 of the cathode 14 thereby makes it possible to keep the anode 13 and the walls 12 of the volume 11 perfectly parallel.

FIG. 4 depicts another embodiment of the invention. The references of FIG. 2 have been conserved for the unchanged elements.

Inside the central hole of the perforated disc 15 of the cathode 14, corresponding to a preferred location zone of the plasma, the intensity of the electrical field E 17 is very intense, and up to five times more intense than in the rest of the cylindrical volume 11. The intensity of the electrical field 17 at this location is such that it may produce sputtering of the anode 13 at this level. This risk is even greater when the supply voltage of the anode 13 is above approximately 3,000 volts. The sputtering of the anode 13 shows stray light emission on the emission spectrum in the form of very wide spectral bands that do not correspond to the types present within the vacuum chamber. These intense stray bands may further mask the optical emission bands characteristic of the types present.

In order to avoid this risk, the anode 13 is insulated from the cathode 14 by a mount 25 made of dielectric material which is inserted in the central hole of the perforated disc 15. Thus the inside of the central hole of the cathode 14 is neutralized, and there is no longer the risk of sputtering of the anode 13, which is cumbersome for spectral measurement. The suppression of this zone poses the problem of slightly reducing the emission of light emitted by the plasma source. However, the possibility of being able to more heavily supply the anode 13 makes it possible to largely compensate for the loss of light, and thus take a measurement in real time (less than one second).

In this embodiment, it is therefore necessary to increase the supply voltage of the electrodes when the pressure of the gases to be analyzed is low, in the order of $10^{-7}$ mbars. However, the application of such voltage is much more important when the pressure is higher, greater than $10^{-5}$ mbar. The intensity of the plasma is then such that the anode again risks sputtering. Furthermore, the molecules cracked by the plasma quickly contaminate by deposit the volume 11 containing the plasma and the optical elements that may be located close to it, and this in less than 24 hours. In order to maintain an advantage at any pressure, a control device 26 for the supply voltage of the anode 13 is installed: when the pressure of the gases to be analyzed increases, the supply voltage of the anode 13 is reduced, and when the pressure decreases, the supply voltage is increased. Thus, one obtains, regardless of the pressure, a sufficiently intense plasma in order to take a measurement in real time, yet sufficiently weak so as to avoid any contamination of the optical elements. The life of the system is consequently increased as pollution by deposit is greatly reduced. This control may be correlated with the ionization current generated in the plasma source or with the intensity of the spectrum, for example with the aid of an optical emission spectrometer. The addition of a control makes it possible to obtain a system able to operate at much higher pressures, which makes it possible to conduct a spectral measurement in a pressure range that may stretch from $10^{-5}$ mbar to 1 mbar. The measurement of the ionization current makes it possible to obtain a measurement of the pressure in this same operating pressure range.

As depicted in FIG. 5, the light emitted by the plasma that passes through the transparent window 40 is collected by the optical collection system 5 and spectrally analyzed by an analysis device 6.

The analysis device 6 for analyzing the light emitted by the plasma is made up of an optical emission spectrometer (OES) 41 associated with a computer 42 optically connected by a fiber 43 which transports the light from the optical collector 5 to the spectrometer 41. Advantageously, the computer 42 is placed with the optical emission spectrometer 41 within the same casing, so as to form a compact integrated control system. This way, the lengths of the cables linking the computer 42 to the optical spectrometer 41 are very short, which makes it possible to guarantee very short gas analysis times (<20 ms). This integrated control system interacts with the fabrication equipment to which it is connected based on the results of the gas analysis. This control system may, for example, shut off the machine's function, or trigger a system for purging the controlled-pressure enclosure 1.

The ionization device 4 is surrounded by a secondary vacuum, and must therefore be separated from the optical acquisition chain 7 which is at atmospheric pressure, by a wall transparent to light. The interface between the vacuum medium 11, in which the plasma is generated, and the outside atmosphere is created here using the transparent window 40 equipped with sealing joints which allow light through. The window 40 is preferentially placed as close as possible to the area emitting the light 44 coming from the plasma, in order to optimize its detection.

The optical collector 5 collects the light emitted by the plasma and causes it to converge upon the end of the optical fiber 45, the other end of which is connected to the input 46 of the optical emission spectrometer 41. The optical collector 5 here comprises at least one converging lens 47 making it possible to collect the light emitted by the plasma. These lenses may be simple (biconvex, plano-convex) or achromatic (so as to bypass chromatic aberrations and thereby improve focusing).

The optical axis of the optical light collection system 5 and the electrodes' axis 18 of revolution are one and the same. The focal distance of the optical system is calculated to be as small as possible in order to optimize convergence, which at the same time reduces the optical system's total form factor.

In order to improve transmission over a precise range of wavelengths, the window 40 and lenses 47 may undergo anti-reflection treatment, such as the application of a thin layer of MgF2 intended to improve transmission over the range of 400-800 nm. In order to achieve optimum transmission over the largest possible range of wavelengths, the window 40 and lenses may be made of 47 materials with special compositions. For example, calcium fluoride may be used, as may fused silica, for which transmission is greater than 90% over the range 200-1000 nm.

Thus, the optical acquisition chain 7 of the inventive gas-analyzing system 2 makes it possible to achieve real-time measurement (measurement time less than 1 second).

In the embodiment depicted in FIG. 6, one of the lenses 50 composing the optical collector 5 may make it possible, if it is abutting a seal 51, to bypass the use of a transparent window, this lens 50 itself serving as an interface separating the vacuum from the atmospheric pressure. The routing of the light from the output of the optical collector 5, which is the point of focusing the light from the source of plasma, onto the input 46 of the spectrometer 41, is achieved by the use of an optical fiber 52, placed behind the lens 50, which collects and guides the light radiation 53. The length of the optical fiber 52 is chosen to be as short as possible (here, about 10 cm) in order to reduce the optical losses within the fiber as much as possible 52.

In one variant embodiment, the optical collector 5 of the light is an optical device whose point of convergence is located at the input slot 46 of the spectrometer 41. This device may be made up of a set of several lenses 50, which makes it possible to improve the convergence. In this situation, the input slot 46 of the optical spectrometer 41 is placed directly upon the point of convergence of the light beam 53. The light is not guided to the optical emission spectrometer by means of an optical fiber, but rather by directly focusing the beam of light 53 onto the input flap 46, as the optical fibers offer less optimal transmission over large ranges of wavelengths.

The invention claimed is:

1. A gas-analyzing system for analyzing gases under pressure on the order of a secondary vacuum, comprising:
a gas-ionization device comprising:
a cathode having conducting walls defining a cylindrical volume and a disc including at least one central through hole;
an anode placed substantially at the centre of the hole; and
a plasma source formed of the anode and the cathode, the plasma being generated in the cylindrical volume by the combined action of an electric field and a magnetic field orthogonal to the electric field;
a system for collecting the light radiation emitted by the plasma;
a cylindrical cavity coaxial to the anode, having a conductance lower than that of the cylindrical volume, arranged between the ionization device and the collecting system; and
an analysis device for the ionized gases including an optical spectrometer for analyzing the evolution of the radiating spectrum.

2. A system according to claim 1, wherein the cathode comprises a perforated disc comprising peripheral transverse holes surrounding a transverse central hole.

3. A system according to claim 1, wherein the diameter d of the cavity is less than the diameter D of the cylindrical volume, the diameter d being adjustable depending on the pressure of the gases to be analyzed.

4. A system according to claim 1, wherein the anode is insulated from the cathode by a mount made of dielectric material inserted in the central hole of the disc of the cathode.

5. System according to claim 4, further comprising a regulating device making it possible to control the supply voltage of the anode upon variation of pressure of the gases to be analyzed.

6. A system according to claim 1, wherein the collecting system comprises at least converging lens, whereby the optical axis and the axis of the electrodes are one and the same.

7. A system according to claim 1, wherein the end of the cavity opposite the cylindrical volume is blocked by a window transparent to the light radiation emitted by the plasma.

8. A system according to claim 1, wherein the end of the cavity opposite the cylindrical volume is blocked by a lens transparent to the light radiation emitted by the plasma.

9. A system according to claim 1, wherein the cavity is disposed on the end of the cylindrical volume such that the pathway of the light radiation is in the same direction, opposite the flow of the pumped gases.

10. A plasma-based semiconductor fabrication machine comprising at least one enclosure containing gases kept in a secondary vacuum, connected to a gas-analyzing system comprising:

a gas-ionization device comprising:
  a cathode having conducting walls defining a cylindrical volume and a disc including at least one central through hole;
  an anode placed substantially at the centre of the hole; and
  a plasma source, the plasma being generated in the cylindrical volume by the combined action of an electric field and a magnetic field orthogonal to the electric field;
a system for collecting the light radiation emitted by the plasma;
a cylindrical cavity coaxial to the anode, having a conductance lower than that of the cylindrical volume, arranged between the ionization device and the collector system; and
an analysis device for the ionized gases including an optical spectrometer for analyzing the evolution of the radiating spectrum;
wherein the ionized gas analysis device comprises an optical emission spectrometer associated with a computer, the optical emission spectrometer and the computer being placed within a shared casing so as to constitute a compact integrated control system, and connected to the machine in order to interact with it depending on the results of the gas analysis.

* * * * *